United States Patent [19]
Shimizu et al.

[11] Patent Number: 6,099,464
[45] Date of Patent: Aug. 8, 2000

[54] BENDING SHEATH FOR PROBE

[75] Inventors: Yoshihito Shimizu, Hachioji; Masashi Abe, Akiruno, both of Japan

[73] Assignee: Olympus Optical Co., Ltd., Tokyo, Japan

[21] Appl. No.: 08/629,047

[22] Filed: Apr. 8, 1996

[30] Foreign Application Priority Data

Apr. 10, 1995 [JP] Japan ................................. 7-083936

[51] Int. Cl.[7] ....................................................... A61B 1/00
[52] U.S. Cl. ......................... 600/104; 600/114; 600/115; 600/121
[58] Field of Search ................................... 600/104, 106, 600/107, 108, 121, 123, 125, 114; 604/95

[56] References Cited

U.S. PATENT DOCUMENTS

| | | | |
|---|---|---|---|
| 1,621,159 | 3/1927 | Evans | 600/104 |
| 4,759,748 | 7/1988 | Reed. | |
| 4,878,853 | 11/1989 | Chin | 600/127 |
| 5,306,245 | 4/1994 | Heaven. | |
| 5,807,306 | 9/1998 | Shapland et al. | 606/21 |
| 5,843,032 | 12/1998 | Kastenhofer | 604/96 |

FOREIGN PATENT DOCUMENTS

| | | |
|---|---|---|
| 64-1292 U | 1/1989 | Japan. |
| 3-99647 | 4/1991 | Japan. |
| 5-38342 | 2/1993 | Japan. |
| 5-269134 | 10/1993 | Japan. |

*Primary Examiner*—John P. Leubecker
*Attorney, Agent, or Firm*—Stevens, Davis, Miller & Mosher, L.L.P.

[57] ABSTRACT

A bending sheath for a probe being inserted in a channel of a forceps of an endoscope inserted in a body cavity of a patient for observing the diseased part thereof is disclosed. The bending sheath comprises a hollow sheath, at least one extended portion extending in the sheath axis direction from the sheath tip portion, and a tip holding member for holding detachably the inserted tip portion of the probe inserted in the sheath.

25 Claims, 15 Drawing Sheets

FIG._2

FIG_4A
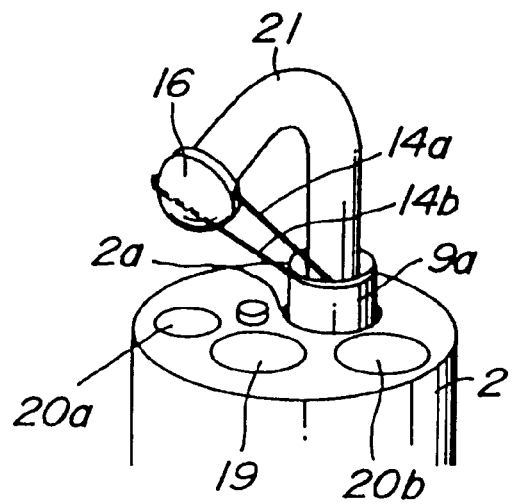
FIG_4B
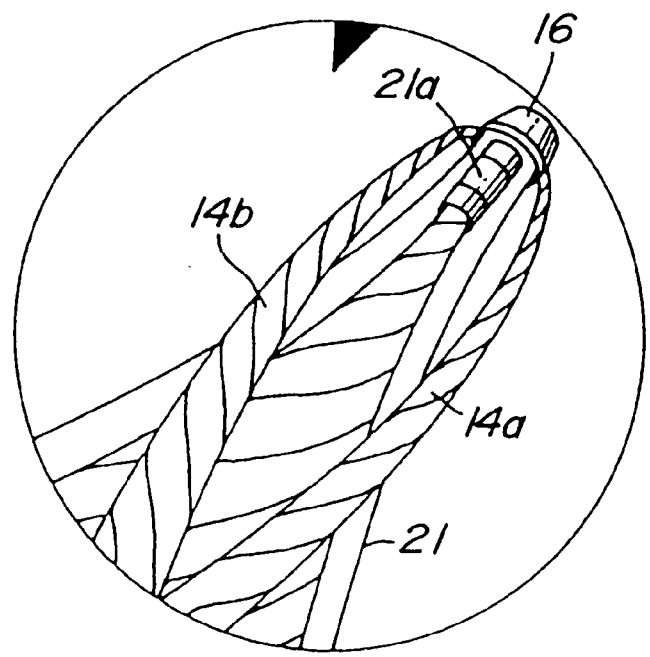

FIG_6
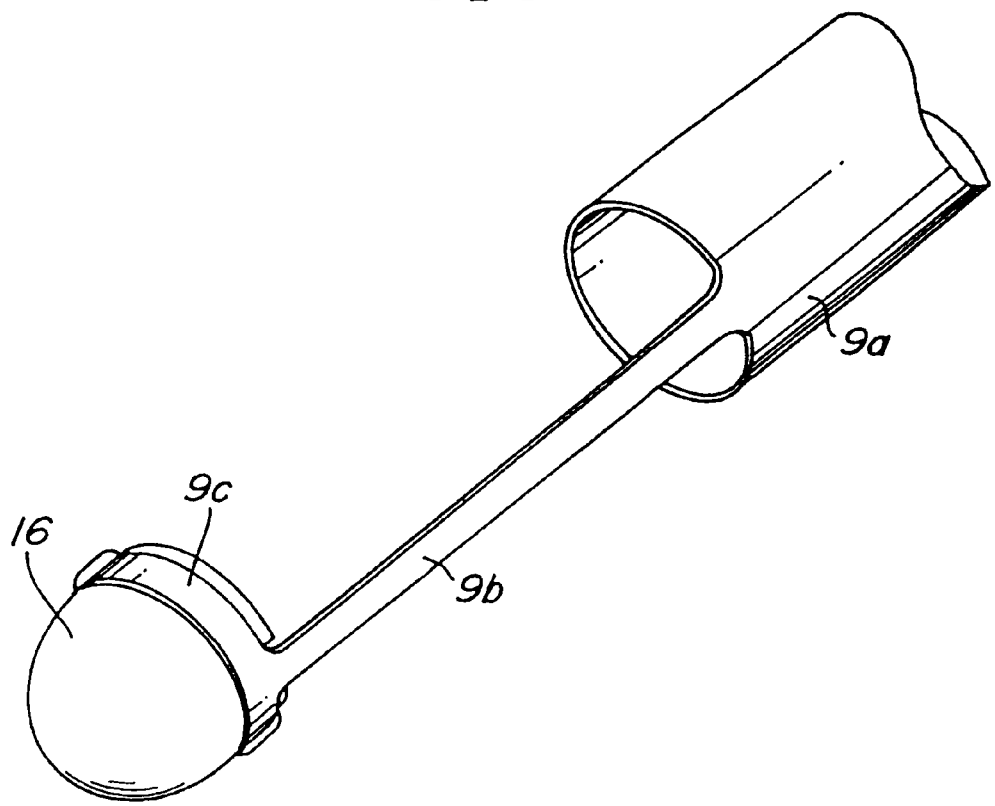
FIG_7
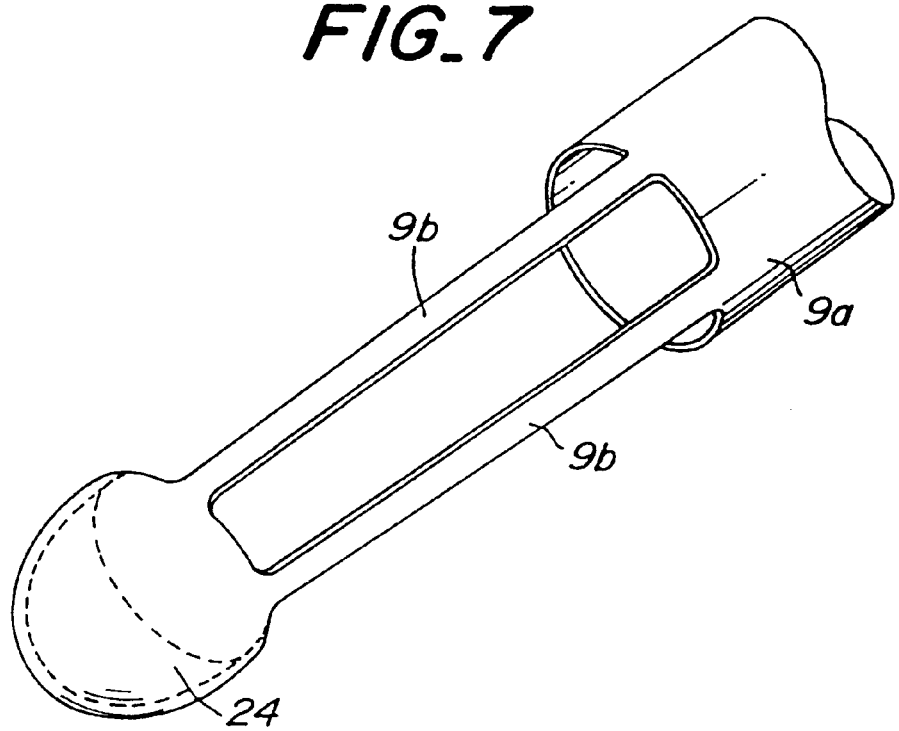

FIG_9

FIG_11

FIG_12

FIG_14

BENDING SHEATH FOR PROBE

BACKGROUND OF THE INVENTION

1. Field of the Invention

The present invention relates to a bending sheath for a probe, by which a tip of the probe such as an ultrasonic probe or a laser probe inserted through a forceps channel of an endoscope inserted in a body cavity is bent.

2. Related Art Statement

Recently, there is developed an operation system in which a diagnosis and an operation in the body cavity are performed with the use of an endoscope. While in accordance with downsizing and diameter reduction of the ultrasonic probe and the laser probe, these probes are inserted through the forceps channel, and then diagnosis of and operation on a diseased part in a body cavity are performed.

In this case, in order to guide the probe such as the ultrasonic probe and the laser probe to the position of diseased part in the body cavity in place, in addition to suitable handling by handling portion of the endoscope, the bending operation of the probe tip portion must be performed properly.

As means for performing bending action of the probe tip properly, there are various methods, such as a method of bending the tip portion of the probe by pulling up a bending wire same as in the bending structure in general endoscope (Japanese Patent Application laid Open No. 38,342/93, first prior example), a method of using the shape memory alloy (Japanese Utility Model Application Laid Open No. 1,292/90, second prior example), and a method of bending the endoscope tip portion by pulling up the wire fixed to the tip portion, or the like. U.S. Pat. No. 5,306,245 (third prior example) discloses a construction that a hinge means is formed by cutting out the wall of an annular member, and an acting wire for performing a bending to the hinge side is provided, and U.S. Pat. No. 4,759,748 (fourth prior example) discloses a construction that a moving tube is inserted into a fixed tube, the tip portion of the moving tube protruded from the fixed tube is connected to a tip portion of the moving tube by a flexible member, and a shrinkage-proof member is provided to the flexible proof member.

Also, Japanese Patent Application laid Open No. 99,647/91 (fifth prior example) discloses a construction that an ultrasonic probe and a wire fixed to the tip portion of the ultrasonic probe are inserted in one catheter, and the probe tip portion is bent by drawing the wire.

Japanese Patent Application laid Open No. 269,134/93 (sixth prior example) discloses a construction that an ultrasonic probe and a beading sheath provided with a bent portion being bent by the pulling of the bending wire on the tip of a hard pipe, are combined.

As a means of detecting bent angle of the bending portion of the endoscope tip portion, a method of providing an encoder to the bending knob of the endoscope proximal end is well known.

However, since the above first prior example requires the radius fining of the bending wire in accordance with the radius fining of the probe, it is feared that the extension and wire breaking due to strength lacking for tension are caused, so that it is difficult to realize radius thinning of the probe, and to perform the action by the bending wire.

The above second prior example requires a driving circuit for driving SMA and means for controlling temperature, so that whole apparatus becomes complicated in construction.

In the above third prior example, since the wire provided to the hinge aide is bent by drawing action and the radius fining of the bending wire is required in accordance with the radius fining of the annular member, it is feared that the extension and wire breaking due to strength lacking for tension are caused, so that it is difficult to realize radius fining of the annular member and to realize an action due to the bending wire.

In the fourth prior example, respective constituent members are formed integrally, so that if a use of these components as a disposable article is taken into consideration, an expensive probe must be disposed together with other components, resulting in an expensive bending sheath.

In the fifth prior example, since the radius fining of the bending wire is required in accordance with the radius fining of the catheter, it is feared that the extension and wire breaking due to strength lacking for tension are caused, so that it is difficult to realize radius fining of the catheter and to realize an action due to the bending wire.

In the sixth prior example, the hard pipe is used, so that it is not a combination of it to the flexible endoscope. Moreover, a safe material for the living body must be utilized.

SUMMARY OF THE INVENTION

It is an object of the present invention to eliminate the above described disadvantages of the conventional bending sheath.

It is another object of the present invention to provide an inexpensive bending sheath for probe capable of combining with respective probes such as ultrasonic probe insertable into the forceps channel of the endoscope and capable of bending the tip portion of the probe with simple construction properly.

According to the present invention, there is provided a bending sheath for a probe being inserted in a channel of a forceps of an endoscope inserted in a body cavity of a patient for observing the diseased part thereof comprising a hollow sheath, at least one extended portion extending in the sheath axis direction from the sheath tip portion, and a tip holding member for holding detachably the inserted tip portion of the probe inserted in the sheath.

According to the present invention, the probe is inserted into the hollow sheath so as to abut the tip portion of the probe to the tip holding member, Under this condition, the probe can be inserted into the insertion section of the endoscope which is inserted in the body cavity.

When the probe is further inserted in the sheath, the probe is bent between the sheath and the tip holding member since the end portion of the probe is biased to the tip holding member.

According to the present invention, the tip portion of the probe can be bent only by forcibly inserting the probe such as ultrasonic probe into the bending sheath. The bending angle of the probe tip portion can be adjusted easily by adjusting the insertion amount of the probe for the bending sheath.

The extending portion can also be detected by the transmitting and receiving of the ultrasonic from the ultrasonic transducer, so that the orientation of the ultrasonic image can be grasped, thereby making the orientation around the diseased part easily.

In an embodiment of the bending sheath for probe according to the present invention, the hollow sheath is a tube formed by a soft resin. In this way, the smooth working for inserting and further forcibly inserting the probe into the sheath can be performed easily.

In a preferable embodiment of the bending sheath according to the present invention, the soft resin forming the hollow sheath is a Teflon (trade name), a high-density polyethylene or a low-density polyethylene or a mixed polyethylene thereof, or a polyimide resin or a polyolefin resin. In this way, the smooth working for inserting and further forcibly inserting the probe into the sheath can be performed easily.

In a further preferable embodiment of the bending sheath according to the present invention, the extension portion is a wire. The wire being the extension portion is a stainless stranded wire, a stainless wire, a gut, or a vegital filature. In this way, when the probe is inserted into the sheath, the tip holding portion can surely be held so as to impart the biasing force to the probe tip portion.

In a preferable embodiment of the bending sheath according to the present invention, the extended portion is formed by two wires having V-shaped extension so as to hold the tip holding member therebetween. In this way, in addition to the fact that when the probe is inserted into the sheath, the tip holding portion can surely be held so as to impart the biasing force to the probe tip portion, even under the condition of bending the probe tip portion, the probe itself and its incidental facilities can easily be recognized by eyes.

In a further preferable embodiment of the bending sheath according to the present invention, the extended portion is integrally formed with the same material as that of the sheath, or is two parallel portions and is integrally formed with the same material as that of the sheath, and is integrally formed with the tip holding member at a tip of the extension portion. In this way, respective members can be formed by one tube, so that simplification and easy assembling of the construction can be tried, or the probe tip portion can be recognized by eyes over the extending portion, if transparent resin is used.

In a further preferable embodiment of the bending sheath according to the present invention, the extended portion is formed so as to bend near the tip holding member, is formed by a wide portion at the side of the sheath and a narrow portion at the side of the tip holding member so as to bend near the tip holding member, and is formed by a low flexible portion at the side of the sheath and a high flexible portion at the side of the tip holding member so as to bend near the tip holding member, In this way, the tip holding member can be positioned near the sheath axis, so that the bending conditions of the probe can be recognized with eyes within the field range of the endoscope.

The tip holding member is formed in the shape of a semi-circle cap, and the cap shaped tip holding member is formed by a stainless steel. In this way, the tip portion of the probe can be held detachably, so that the probe tip portion can be bent smoothly. Moreover, the probe tip portion can properly be bent smoothly, without deforming the tip holding member.

The bending sheath further comprises a guide member having thin diameter extended at the tip portion of the tip holding member and on the sheath axis. In this way, when the bending sheath is inserted into the isthmus of the body cavity and the duodenum papillary, the sheath can easily be inserted thereinto through the guide member.

The guide member is formed in a hollow shape. In this way, regardless of having the guide member, the tip receiving portion can be lightened and thus treating can be improved.

The hollow sheath is formed by a rotatable coil shafts In this way, the probe tip portion capable of bending only in one direction can be bent in other direction by rotating the coil shaft.

The rotatable coil shaft forming the hollow sheath is formed by multiple coil shaft layers each being formed by a helical coil consisting of multiple wires. The coil shaft forming the hollow sheath is formed by triple coil shaft layers each being formed by a helical coil consisting of five wires. In this way, the coil shaft having good rotating transmissivity in forward and reverse directions can be obtained, so that the bending direction of the probe tip can be changed properly.

The hollow sheath is formed by a rotatable torque transmission tube of resin. The rotatable torque transmission tube of resin forming the hollow sheath is formed by an embedded metal, silk, and cotton mesh member. In this way, the probe tip portion capable of bending only in one direction can be bent in other direction by rotating the torque transmission tube of resin. Also, the hollow sheath, the extended portion and the tip holding member can be integrally formed, thereby making manufacturing cost of the bending sheath inexpensive.

The tip holding member is provided with a reflecting portion at its portion. The reflecting portion is formed by making a surface roughness large. In this way, the bent extent of the probe tip can easily be grasped in accordance with the reflecting extent of the reflecting portion.

The reflecting portion is formed by a prism or a mirror. In this way, the bent extent of the probe tip can easily be grasped by discriminating the reflected light or the color thereof.

The tip holding member is rotatably connected to the extended portion through a link mechanism. In this way, the bent portion of the probe tip can be recognized at the center of field range of the endoscope.

The bending sheath for a probe being inserted in a channel of a forceps of an endoscope inserted in a body cavity of a patient for observing the diseased part thereof, comprises a hollow sheath, a bellows member capable of expansion and contraction continuously provided to the tip and portion of the sheath, a fixing portion continuously provided to the tip portion of the bellows and for fixing the tip portion of the probe inserted in the hollow sheath, at least one extended portion fixed to the fixing portion at its one end and extended to a proximal end in the sheath, and an extended acting means for adding or releasing a biasing force to or from the extended portion. The extended portion is formed by two or four portion. In this way, in case of combining the sheath with the endoscope the probe tip can be bent in the required direction by selecting plural extended portions while recognizing the bending direction within the field range of the endoscope, without using the method of rotating the bending sheath.

The fixing portion is formed by drawing the tip portion of the sheath so as to engage a flange portion formed on the probe. In this case, the probe is inserted into the sheath so as to engage the flange to the fixing portion, thereby obtaining a simple fixation.

The probe inserted in the hollow sheath is an apparatus for irradiating energy having directivity. In this way, the energy irradiation can be performed properly by bending the probe tip portion near the diseased portion of the patient.

The apparatus for irradiating energy inserted in the hollow sheath is an ultrasonic probe or a laser probe. The probe inserted in the hollow sheath is a treating unit of a punch biopsy. In this way, the treating for diseased portion, that is, the irradiation of the ultrasonic or laser can be performed by bending the probe tip portion near the diseased portion of the patient.

The bending sheath for a probe being inserted in a channel of a forceps of an endoscope inserted in a body cavity of a patient for observing the diseased part thereof, comprising a hollow sheath, at least one extended portion extending in the sheath axis direction from the sheath tip portion, a tip holding member for holding detachably the inserted tip portion of the probe inserted in the sheath, and a balloon provided between the sheath and the tip holding member. In this way, the distance between the bent probe and the wall of organism is held constantly, so that good ultrasonic image can be obtained in the case of the ultrasonic probe. If the bending sheath is used together with the direct sight endoscope ultrasonic diagnosis can be performed by the balloon method under the state opposite to the diseased portion.

BRIEF DESCRIPTION OF THE DRAWINGS

FIG. 4a is a perspective view showing the utilizing state of second embodiment of the bending sheath according to the present invention;

FIG. 4b is an enlarged view showing the probe tip through an observing optical system;

FIG. 6 is a partial perspective view showing third embodiment of the bending sheath according to the present invention;

FIG. 7 is a partial perspective view showing fourth embodiment of the bending sheath according to the present invention;

DETAILED EXPLANATION OF THE PREFERRED EMBODIMENT

Figure 1:
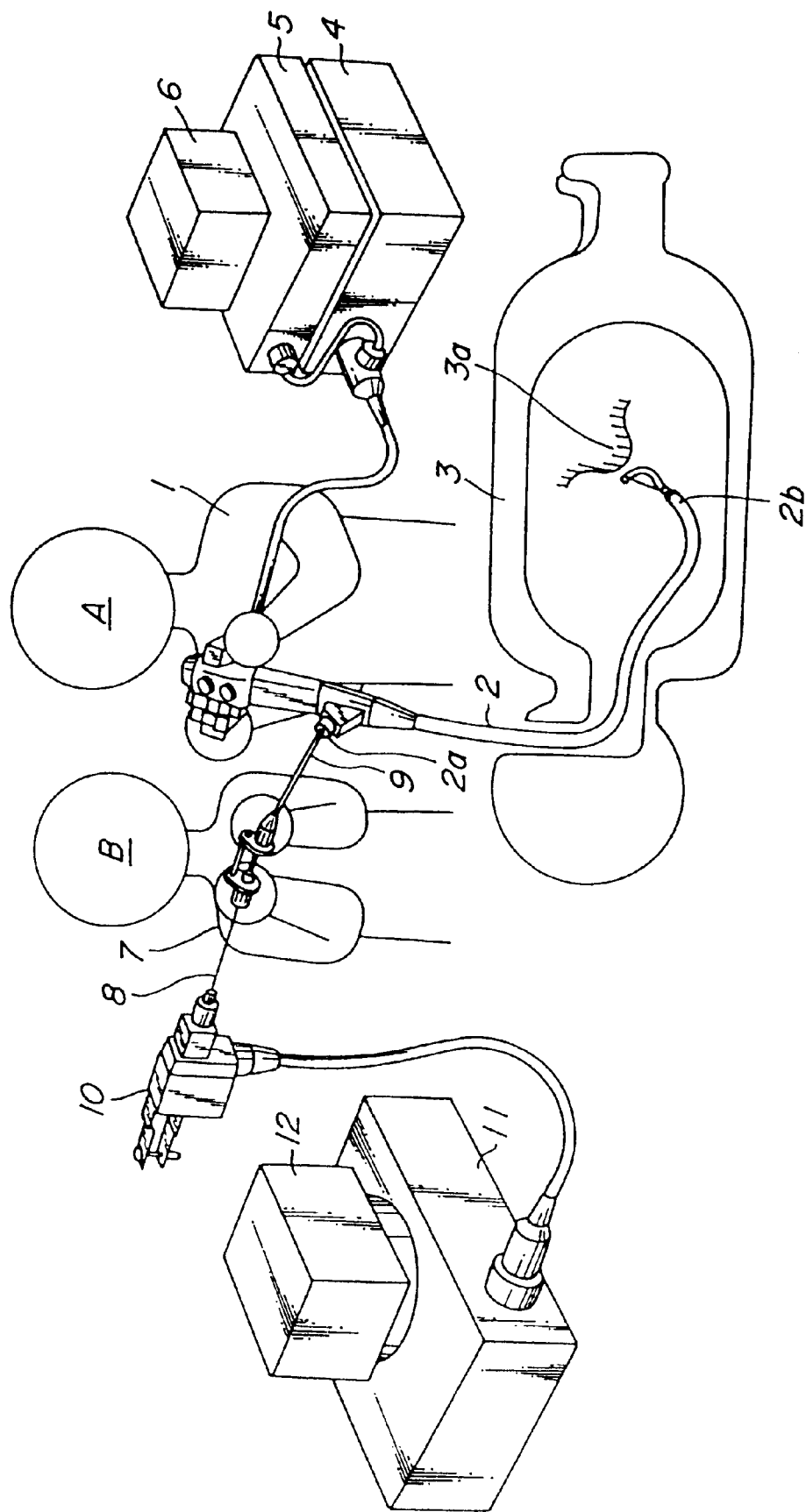
FIGS. 1 is an explanatory view showing the state of performing a diagnosis to a patient by an endoscope using a bending sheath according to the present invention.

Now to the drawings, there are shown various embodiments of a bending sheath according to the present invention. Like parts are shown by corresponding reference characters throughout several views of the drawings.

Figure 2:
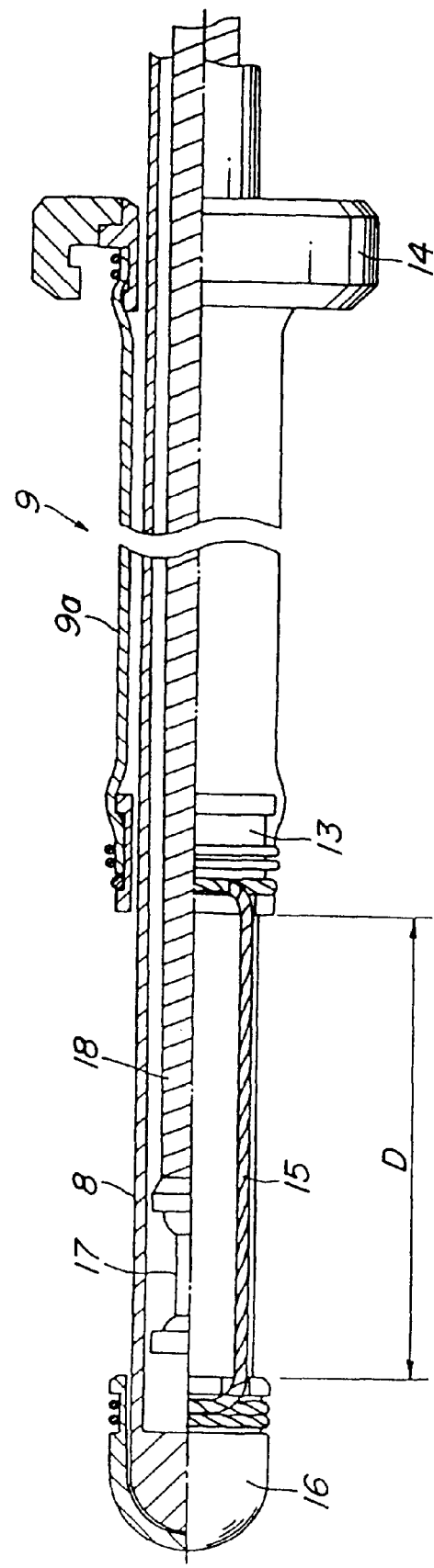
FIG. 2 is an elevational view partly in section showing a tip of an ultrasonic probe and a bending sheath of first embodiment of the present invention.
Figure 3:
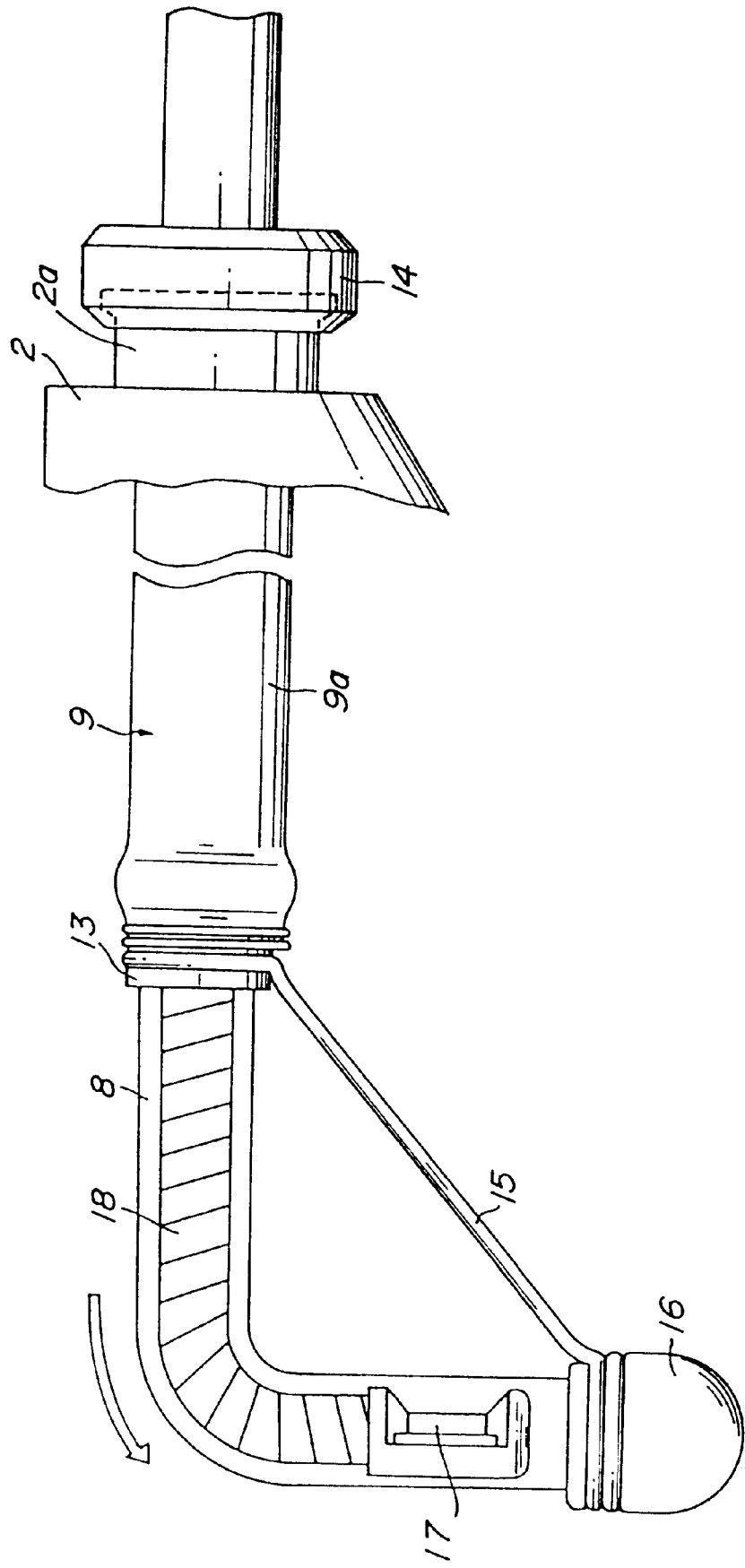
FIG. 3 Is a side view showing a bending state of the tip portion of the ultrasonic probe.

FIGS. 1 to 3 show first embodiment of a bending sheath according to the present invention. FIG. 1 shows the state of performing a diagnosis to a patient by an endoscope using a bending sheath according to the present invention. As shown in FIG. 1, an operator A (1) inserts an insertion section of an endoscope 2 such as a video oscilloscope or the like into a body cavity of a patient so as to lead a tip 2b of the insertion section near a diseased portion 3a in the body cavity.

The endoscope 2 is connected to a light source 4, a video processor 5 and a scope monitor 6 in such a manner that an observation by endoscope can be performed and an image of the subject can be displayed.

While an operator B (7) mounts an ultrasonic probe (probe) 8 on a bending sheath 9, and inserts it into a forceps channel from a forceps hole 2a of the endoscope 2, and as shown in FIG. 1, the tip of the ultrasonic probe 8 is projected to the diseased portion 3a from the tip portion of the insertion section.

The ultrasonic probe 8 is connected to an ultrasonic observing apparatus 11 and an ultrasonic monitor 12 through a driving unit 10 in such a manner that the deep portion of the body cavity can be observed by ultrasonic wave.

That is, the ultrasonic probe 8 is provided at its tip portion with an ultrasonic transducer and the ultrasonic tomographic image can be displayed on the ultrasonic monitor 12 to obtain it by transmitting and receiving the ultrasonic wave to and from the diseased portion.

The operators A(1) and B(7) are acted in such a manner that the tip of the ultrasonic probe 8 can be bent by inserting it into the bending sheath 9, thereby obtaining the ultrasonic tomographic image in the desired direction while bending the tip of the probe 8.

FIG. 2 is a sectional view showing the tip portion of the bending sheath 9 and the ultrasonic probe 8. A fixing base 13 has one end, to which an outer sheath 9a of Teflon (trade name) such as PTFE (polytetrafluoroethylene) or TFE (tetrafluoroethylene) is provided inside, and has the other end, to which a forceps channel base 14 is provided. The fixing base 13 is provided with a metal stranded wire (extrusion) 15 which is wound on the fixing base at its one end and is fixed thereto by soldering. The other end of the wire 15 is wound and fixed by soldering on and to a metal cap (the tip holding member) 16 which is provided at the port apart from the front end of the outer sheath 9a.

The outer sheath 9a is not limited to the tube of Teflon, and may be made a tubular sheath capable of inserting and extending the probe therein and therethrough, and thus the material of the tubular sheath may be a high-density polyethylene, a low-density polyethylene, a mixed polyethylene, a polyurethane, a polyimide, and a polyolefin or the like.

The wire 15 is a metal stranded wire, but as long as having constant tensile strength, a stainless stranded wire, a stainless solid (single) wire, a piano wire, or a tungsten wire may be utilized. As such wire, not only the metal but also a gut such as polyethylene and nylon, a silk yarn, and cotton yarn. The utilization of these gut, silk yarn and cotton yarn can suppress an ultrasonic echo from the wire lower.

The distance D between the metal cap 16 and the fixing base 13 which are attached to the wire 15, corresponds to a portion exposing the tip of the ultrasonic probe 8. If the probe being combined to the bending sheath 9 is used as the ultrasonic probe 8, the distance D is determined so as to expose a ultrasonic transducer 17 and a part of a flexible shaft 18 sufficiently. In practice, this distance D is substantially 20 mm to 30 mm.

The function and effect of this embodiment constructed above is now described. At first, as is shown in FIG. 2, the ultrasonic probe 8 is inserted in the forceps channel base 14 until that the tip portion of the probe 8 is abutted to the inner wall of the cap 16 of the bending sheath 9. Under this condition, the probe is inserted in the forceps channel 2a of the endoscope 2. Then, the forceps channel base 14 is mounted and fixed in the forceps channel 2a of the endoscope 2. FIG. 3 shows conditions that in this way, the ultrasonic probe 8 and the bending sheath 9 are inserted in the forceps channel of the endoscope, In this embodiment, in the proximal end of the bending probe 9, the forceps channel base 14 is mounted on and fixed to the forceps channel 2a of the endoscope 2, but as shown in FIG. 1, instead thereof, the operator B(7) holds and treats the ultrasonic probe 8 and the bending sheath 9.

When the ultrasonic probe 8 is further inserted forcibly for the bending sheath 9, then as shown in FIG. 3, the tip portion of the ultrasonic probe 8 is bent between the fixing base 13 and the cap 16, since the probe tip portion is biased to the cap 16 secured to wire 15.

As shown in FIG. 1, therefore, the ultrasonic probe 8 is positioned under the condition that the tip thereof is bent for the diseased portion in the body cavity, so that the ultrasonic tomographic image can be obtained in the desired direction, At the time of finishing the ultrasonic observation, the ultrasonic probe 8 is again drawn a bit to make its tip straight and then to draw back in the endoscope 2.

In this embodiment, the probe to be combined with the bending probe is the ultrasonic probe 8, but the present invention is not limited thereto, if the bending of the tip portion is required at the time of utilization thereof, the probe may be a laser probe, a microwave irradiating probe, a general treating unit, or a catheter.

As described above, in the present embodiment, the tip portion of the probe can be bent properly only by forcibly inserting the probe such as ultrasonic probe into the bending sheath. The bending angle of the probe tip portion can be adjusted easily by adjusting the insertion amount of the probe for the bending sheath.

The wire can also be detected by the transmitting and receiving of the ultrasonic waves from the ultrasonic transducer, so that the orientation of the ultrasonic image can be grasped, thereby making the orientation around the diseased part easily.

FIGS. 4a, b and 5 show a second embodiment of the bending sheath, in this embodiment, the elements corresponding to those of the first embodiment are made the same characters.

As shown in FIG. 4a, in this embodiment, two wires 14a, 14b extended from the fixing base, to which the outer sheath 9a is secured, are provided to have a V shaped extension from the fixing base so as to hold the cap 16 between V shaped extensions.

The endoscope 2 is provided with an observation optical System 19 and illumination optical systems 20a, 20b. FIG. 4b chows a condition that the tip portion of the probe 21 is observed through the observation optical system 19. The other construction is the same as that of the first embodiment.

The function and effect of this embodiment constructed above is the same as that of the first embodiment. That is, the probe 21 is inserted in the forceps channel base until that the tip portion or the probe 21 is abutted to the inner wall of the cap 16 of the bending sheath. Under this condition, the probe is inserted in the forceps channel of the endoscope 2. Then, the forceps channel base is mounted and fixed in the forceps channel of the endoscope 2.

When the probe 21 is forcibly inserted for the bending sheath, then the tip portion of the probe 21 is bent between the fixing base and the cap 16, since the tip of the probe 21 is biased to the cap 16 secured to the wires 14a, 14b.

As described above, as in the same manner as the first embodiment, the tip portion of the probe can be bent properly only by forcibly inserting the probe such as ultrasonic probe for the bending sheath. The bending angle of the probe tip portion can also be adjusted easily by adjusting the insertion amount of the probe for the bending sheath.

As Shown in FIG. 4b, according to the present embodiment, two wires 14a, 14b are provided in such a manner that these wires have a V shaped spread portion extended from the fixing base so as to hold the cap 16 and the sensor 21a between the wires, so that the probe itself 21 and the sensor 21a can easily be recognized with eyes, even under the condition that the tip of the probe 21 is bent.

Figure 5A:
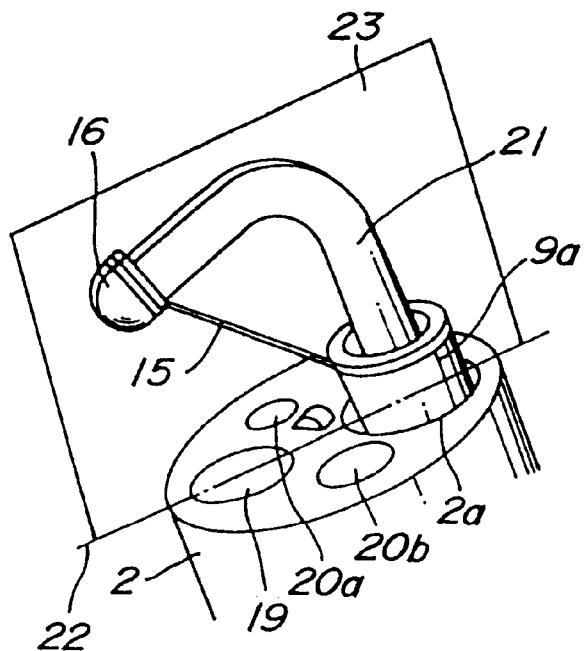
FIG. 5a is a perspective view showing the utilizing state of comparison embodiment to the second embodiment of the bending sheath.
Figure 5B:
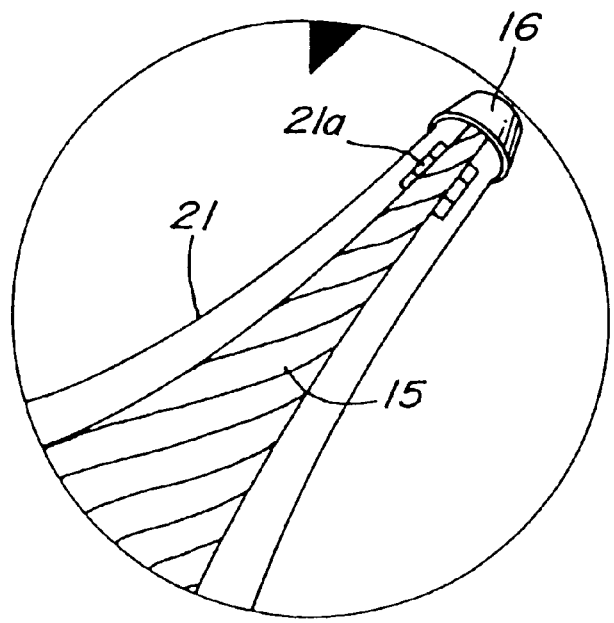
FIG. 5b is an enlarged view showing the probe tip through an observing optical system.

That is, as shown in FIG. 5, when one wire 15 is utilized, if the probe 21 is bent in a plane 23 perpendicular to the tip plane of the endoscope including an axis line 22 that connects respective centers of the observation optical system 19 and the forceps channel 2a at tip portion of the endoscope 2, it is difficult to recognize the probe tip by eyes, in case of observing the diseased portion of the patient, since the tip is hindered by the wire 15.

Moreover, if the wire is cut out by some cause or other, it is feared that the cap 16 may be dropped out in the body cavity, but in this embodiment, even if one of the wires is cut out, such drop-out of the cap 16 can be prevented, since the other wire holds the cap 16.

FIG. 6 shows third embodiment of the bending sheath according to the present invention. In this embodiment, an outer sheath 9a of Teflon an extended portion 9b corresponding to the wire and an annular portion 9c provided at the tip of the extended portion 9b are formed integrally. The cap 16 is fitted in and secured to the annular portion 9c. The other construction is the same as that of the first embodiment, so that its detailed explanation is omitted.

The function and effect of this embodiment constructed as described above is the same as those of the first embodiment. That is, when the probe is inserted in the forceps channel base, the tip portion thereof is abutted to the inner wall of the cap 16 of the bending sheath provided the extended portion 9b and the annular portion 9c. Under this condition, the probe is inserted in the forceps channel of the endoscope 2.

When the probe 21 is further forcibly inserted for the bending sheath, then the tip portion of the probe 21 abutted to the extended portion 9b and exposed from the outer sheath 9a, is bent, since the tip of the probe 21 is biased to the cap 15 integrally formed to the extended portion 9b.

As described above, in this embodiment as in the same manner as the first embodiment, the tip portion of the probe can be bent only by forcibly inserting the probe such as ultrasonic probe for the bending sheath. The bending angle of the probe tip portion can also be adjusted easily by adjusting the insertion amount of the probe for the bending sheath.

According to the present invention, also, the member corresponding to the wire can be integrally formed by notching the outer sheath, so that the fixing base and the wire can be omitted, and thus the assembly work becomes simply, as well as the producing cost can be made largely decreased.

The extended portion and the outer sheath can be formed by the same material, so that the extended portion may also be made transparent by selecting synthetic resin as such a material.

It is natural that plural number of the extended portions may be utilized within a range that the bending of the probe tip is not prevented, and the outer sheath may be formed by polyethylene or the like in addition of Teflon, as long as the tube has proper tensile strength.

FIG. 7 shows fourth embodiment of the bending sheath according to the present invention. In this embodiment, the outer sheath 9a is notched to form two parallel extended portions 9b, and the tip portion of the extended portions 9b are provided with a cap 24 by thermal forming.

The number of the extended portion 9b is not limited to two, but may be made one. The cap portion 24 is formed in the condition that the tip thereof is closed, but as long as the probe combined thereto is biased, it must not always be made a closed form, and may be made only a tapered form. The other construction is the same as that of the first embodiment, so that its detailed explanation is omitted.

The function and effect of this embodiment constructed as described above is the same as those of the first embodiment. That is, when the probe is inserted in the forceps channel base, the tip portion thereof is abutted to the inner wall of the cap 24 of the bending sheath 9a provided through the extended portion 9b. Under this condition, the probe is inserted in the forceps channel of the endoscope, and projected until the extended portion 9b is exposed from the tip of the endoscope.

When the probe is further forcibly inserted for the bending sheath, then the tip portion of the probe abutted to the extended portion 9b and exposed from the outer sheath 9a, is bent, since the tip of the probe is biased to the cap 24 integrally formed to the extended portion 9b.

As described above, in this embodiment as in the same manner as the first embodiment, the tip portion of the probe can be bent only by forcibly inserting the probe such as ultrasonic probe for the bending sheath. The bending angle of the probe tip portion can also be adjusted easily by adjusting the insertion amount of the probe for the bending sheath.

According to the present invention, also, the member corresponding to the wire can be integrally formed by notching the outer sheath, so that respective members can be constructed by one tube, since the cap 24 is formed at the tip of the member by thermal forming, and thus the assembly work becomes simple, as well as the producing cost can be made largely decreased.

The extended portion and the outer sheath can be formed by the same material, so that the extended portion may also be made transparent by selecting synthetic resin as such a material. Therefore, even if one extended portion in provided, the probe tip portion can be recognized with eyes over the extended portion within the field of the endoscope.

Moreover, the member corresponding to the wire need not be connected to the extended portion 9a and the cap 24, so that the drop out of the cap does not occur, resulting in an improvement of the safety.

Figure 8:
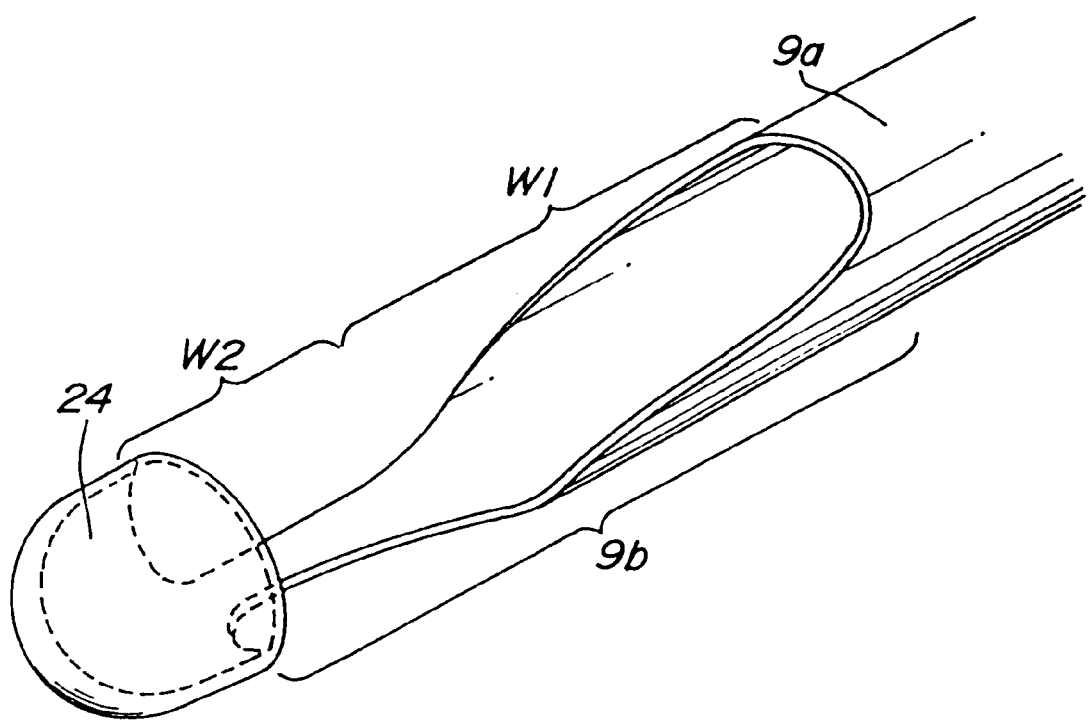
FIG. 8 is a partial perspective view showing fifth embodiment of the bending sheath according to the present invention.
Figure 9:
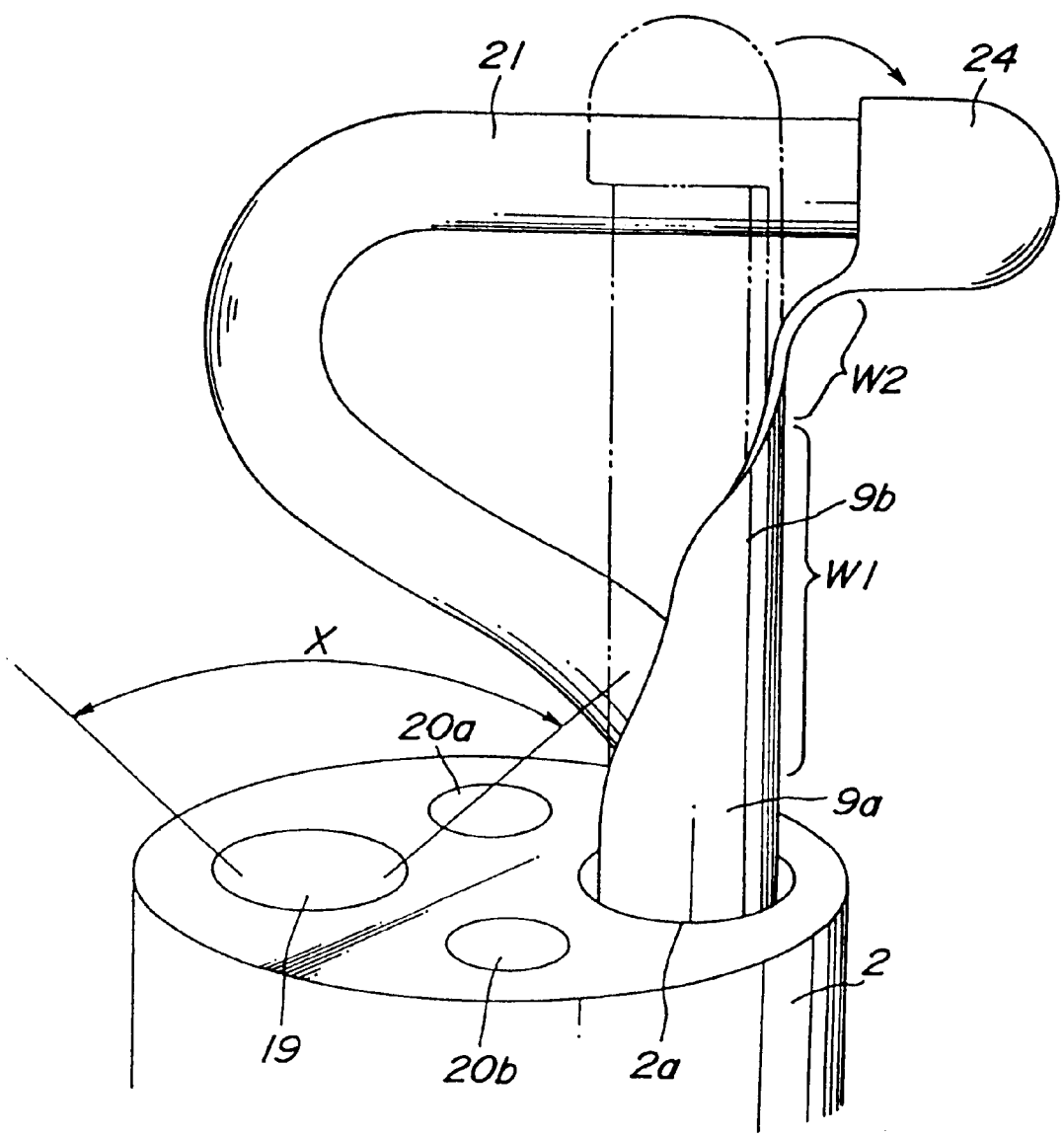
FIG. 9 is an explanatory view showing the utilizing state of fifth embodiment of the bending sheath according to the present invention.

FIGS. 8 and 9 show a fifth embodiment of the bending sheath according to the present invention. In this embodiment, the outer sheath 9a is provided with a taper extended portion 9b continuously and integrally formed thereto. The taper extended portion comprises a wide width portion W1 positioned at the side of the outer sheath 9a and a narrow width portion W2 positioned at the side of the cap 24. This narrow width portion has bending function. Alternately, the wide width portion W1 may be formed by a small flexible material and the narrow width portion W2 may be formed by large flexible material. In this way, the same bending function can also be obtained. The other construction is the same as that of first embodiment, so that its detailed explanation is omitted.

The function and effect of this embodiment constructed as described above is the same as those of the first embodiment. That is, when the probe 21 is inserted in the forceps channel base, the tip portion thereof is abutted to the inner wall of the cap 24 at the tip of the bending sheath 9a provided through the extended portion 9b. Under this condition, the probe is inserted in the forceps channel 2a of the endoscope 2, and projected until the extended portion 9b is exposed from the tip of the endoscope.

When the probe 21 is further forcibly inserted for the bending sheath, then the tip portion of the probe 21 abutted to the extended portion 9b and exposed from the outer sheath 9a, is bent, since the tip of the probe 21 is biased to the cap 24 at the tip of the extended portion 9b.

In this case, the extended portion 9b is bent only at the place of the narrow width portion W2, so that the cap, that is, the tip of the probe can be positioned on the axis of the outer sheath 9a. Therefore, as shown in FIG. 9, the bent state can be observed at the center of field of the observation optical system 19 provided in the endoscope 2.

As described above, in this embodiment as in the same manner as the first embodiment, the tip portion of the probe can be bent only by forcibly inserting the probe such as ultrasonic probe for the bending sheath. The bending angle of the probe tip portion can also be adjusted easily by adjusting the insertion amount of the probe for the bending sheath.

The extended portion 9b is bent at the narrow width portion W2, so that the cap 24 biasing the probe 21 can be positioned near an axis of the outer sheath 9a, and thus the bent portion of the probe 21 can be observed at the center of the endoscope field X as shown in FIG. 9. Therefore, even in any bending direction of the probe 21, the tip of the probe 21 can be recognized with eyes without departing the field X of the endoscope.

Figure 10:
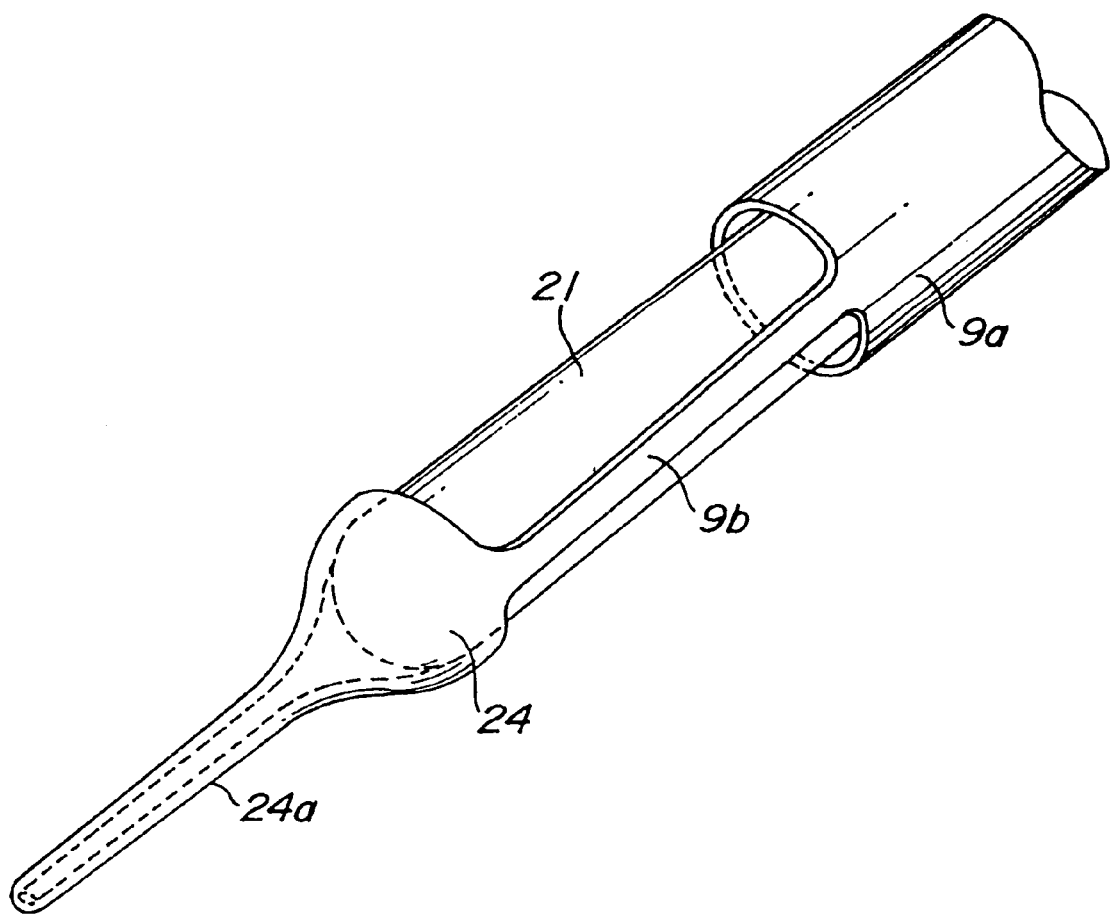
FIG. 10 is a partial perspective view showing sixth embodiment of the bending sheath according to the present invention.

FIG. 10 shows a sixth embodiment of the bending sheath according to the present invention. In this embodiment, the extended portion 9b is formed by notching the outer sheath 9a and the tip portion of the extended portion 9b is provided a cap 24 formed by a thermal forming, a cutting work or a mold forming and the like, and a guide member 24a of thin diameter extending on the outer sheath axis, is formed. This guide member 24a may also be formed in the hollow shape.

As a material of the outer sheath 9a, if thermal plastic resin, such as Teflon and polyethylene or the like is utilized, the guide member 24a of thin diameter which is extended on the outer sheath axis can be formed by proper heat adding and by pulling treatment, so that the bending sheath can be manufactured with low coat without requiring of special mold.

The extended portion 9b may be formed so as to have the wide width portion and the narrow width portion, which are integrally formed as a continuous body, as in the above fifth embodiment, and may be formed as plural extended portions 9b as in the fourth embodiment, The guide portion 24a may also be formed so as to open the tip portion thereof, and the guide wire may be constructed insertably, or another guide wire may be secured to the tip of the cap. The other construction is the same as that of the first embodiment.

The function and effect of this embodiment constructed as described above is the same as those of the first embodiment. That is, when the probe is inserted in the forceps channel base, the tip portion of the probe is abutted to the Inner wall of the cap 24 at the tip of the outer sheath 9a provided through the extended portion 9b. Under this condition, the probe is inserted in the forceps channel 2a of the endoscope 2, and the forceps channel base is mounted on and secured to the forceps channel of the endoscope. When the bending sheath is inserted in an isthmus of the body cavity and a duodenum papillary, such a guide portion 24a is inserted therein as a guide.

When the probe is further forcibly inserted for the bending sheath, then the tip portion of the probe abutted to the extended portion 9b and exposed from the outer sheath 9a, is bent, since the tip of the probe is biased to the cap 24 integrally formed to the extended portion 9b.

As described above, in this embodiment as in the same manner as the first embodiment, the tip portion of the probe can be bent only by forcibly inserting the probe such as ultrasonic probe for the bending sheath. The bending angle of the probe tip portion can also be adjusted easily by adjusting the insertion amount of the probe for the bending sheath.

Moreover, the guide member 24a is formed on the tip portion of the bending sheath, so that when the bending sheath is inserted in the isthmus of the body cavity and the duodenum papillary, the guide member 24a can easily be inserted as a guide. In this way, when the ultrasonic probe is used as a probe, the ultrasonic image can be obtained at the center of the isthmus of the body cavity. Moreover, the tip portion of the probe can be bent, so that the ultrasonic image diagnosis can be performed under the proper condition by adjusting incident angle of the ultrasonic wave for the inner wall of the body cavity. Even when a laser probe and a thermotherapy probe due to microwave or the like are used as a probe, the bending sheath according to this embodiment can be functioned under the proper condition.

Figure 11:
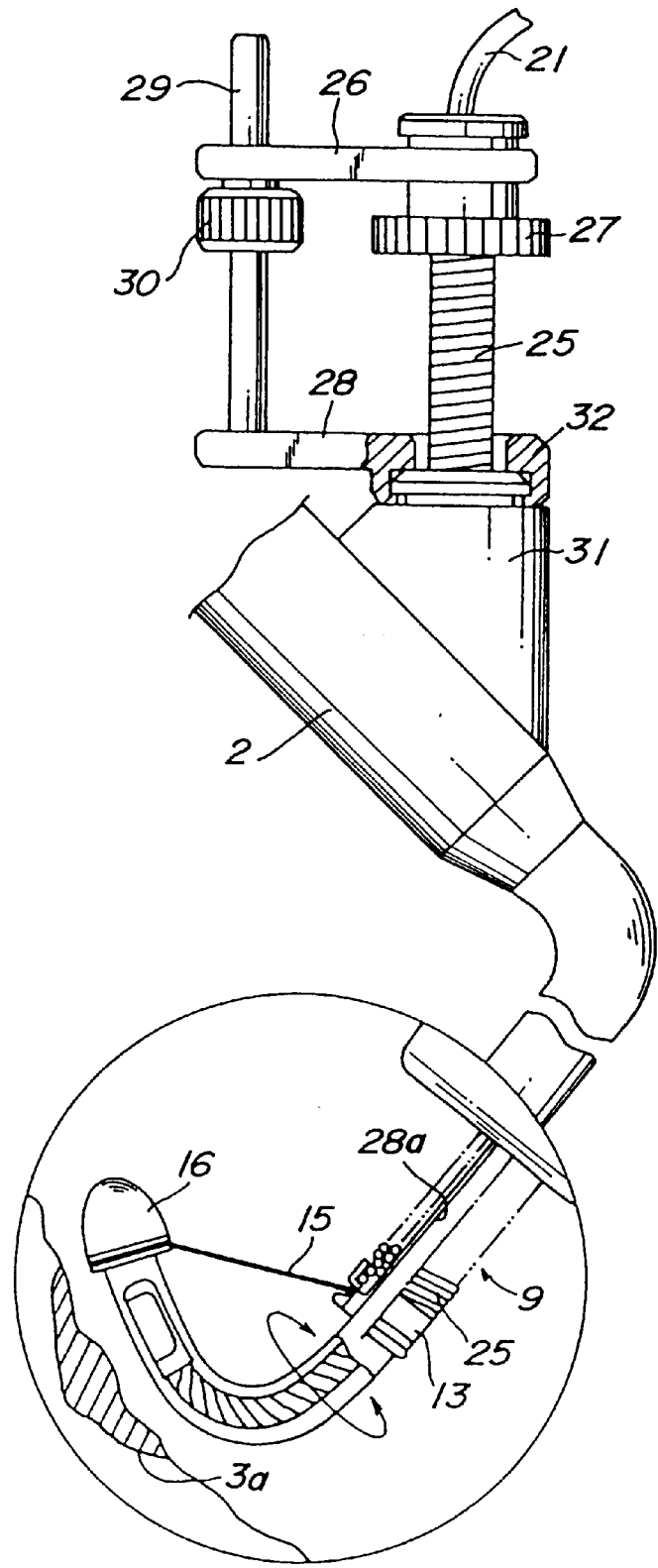
FIG. 11 is a partially expanded side view showing the utilizing state of seventh embodiment of the bending sheath according to the present invention.

FIG. 11 shows a seventh embodiment of the bending sheath according to the present invention. In this Figure, the tip portion of the probe and bending sheath is shown as enlarged figure. In this embodiment, the fixing base 13 is secured to the tip side of a coil shaft 25 having inner diameter capable of inserting the probe 21 by soft soldering, hard soldering, cementing or the like. This fixing base 13 is provided with a cap 16 through at least one wire 15.

The coil shaft 25 is fitted rotatably to a carriage 26 at its proximal end through a rotating knob 27. A shrinkage-proof wire 28a such as stainless steel wire or a cabler and the like is stretched between the fixing base 13 and the rotating knob 27 at inner side of the coil shaft 25.

The carriage 26 is held movably/fixdably for a supporting bar member 29 integrally secured to a fixing unit 28 with cement, through a fixing knob 30, in the axial direction of the supporting bar member. The fixing unit 28 is provided with a detachable member 32 mounted detachably to a forceps channel 31 of the endoscope 2.

The rotatable coil shaft 25 is formed by multiple coil shaft layers each being formed by a helical coil consisting of multiple wires, so as to improve rotation transmissibility, particularly, may be formed by triple coil shaft layers each being formed by a helical coil consisting of five wires, so as to perform rotation in forward and reverse directions. However, as long as the rotation transmissibility is surely obtained, the rotatable coil shaft 25 is not limited to the multiple coil shaft layers each being formed by a helical coil consisting of multiple wires.

As long as the sheath has good rotation transmissibility, a rotatable torque transmission tube of resin, such as Teflon or polyethylene having stainless, silk, and cotton mesh member embedded therein, instead of the coil shaft.

If resin tube having silk mesh member embedded therein is used, the outer sheath 9a, the extended portion 9b and the cap 24 can be formed integrally, so that the manufacturing cost can be decreased.

The function and effect of this embodiment constructed as described above is described hereinafter. That is, when the probe 21 is inserted in the bending sheath 9, the tip portion thereof is abutted to the cap 16. Then, the bending sheath 9 combined with the probe 21 is inserted into the endoscope 2 from the forceps channel 31 and the fixing unit 28 is mounted to the forceps channel 31 through the detachable portion 32.

Then, the fixing knob 30 is released and the carriage 26 is moved, and then the projection degree or extent of the bending sheath 9 from the tip of the endoscope 2 is adjusted and the fixing knob 30 is fastened at the desired position, thereby fixing the carriage 26.

Then, the bending sheath 9 is projected in the body cavity, and then the probe 21 is forcibly inserted for the bending sheath 9, while confirming the diseased portion 3a of the patient 3 by the endoscope 2, thereby bending the tip portion of the probe to the required angle. In this case, the bending direction of the probe tip portion is limited to the given direction, but when the rotating knob 27 provided integrally to the coil shaft 25 is provided, the direction of the probe can optionally be changed as shown in the circular enlarged view of FIG. 11, and thus the direction of the wire 15 for the coil shaft 25 is changed, so that the bending direction can be set optionally.

As described above, in this embodiment as in the same manner as the first embodiment, the tip portion of the probe can be bent only by forcibly inserting the probe such as ultrasonic probe for the bending sheath. The bending angle of the probe tip portion can also be adjusted easily by adjusting the insertion amount of the probe for the bending sheath.

The bending direction of the probe tip portion is generally limited in one direction, but this bending direction may be changed by rotating the coil shaft 25 itself. Moreover, the direction of the probe 21 can be changed without moving the field of the endoscope including the diseased portion 3a, so that the operationality can be improved.

Also, the ultrasonic probe is used as a probe, the forward scanning of the ultrasonic beam can be performed by bending the bending sheath 9 substantially 90 degrees, and the ultrasonic scanning can be performed fully within the field of the endoscope by rotating the probe tip bent with the rotating knob 27 under the constant endoscope field.

Moreover, the carriage 26 is made slidably, the projection amount of the probe 21 from the endoscope tip portion can easily be adjusted only by the operator of the endoscope. In this way, the bending of the prober the adjusting of the bending direction and the adjusting of the projection amount can be performed by one operator, so that the bending sheath 9 of well operationality can be obtained. Also, it is as a matter of course that the bending sheath 9 may be operated by the other operator as in the first embodiment, instead of mounting it to the forceps channel 31.

Figure 12:
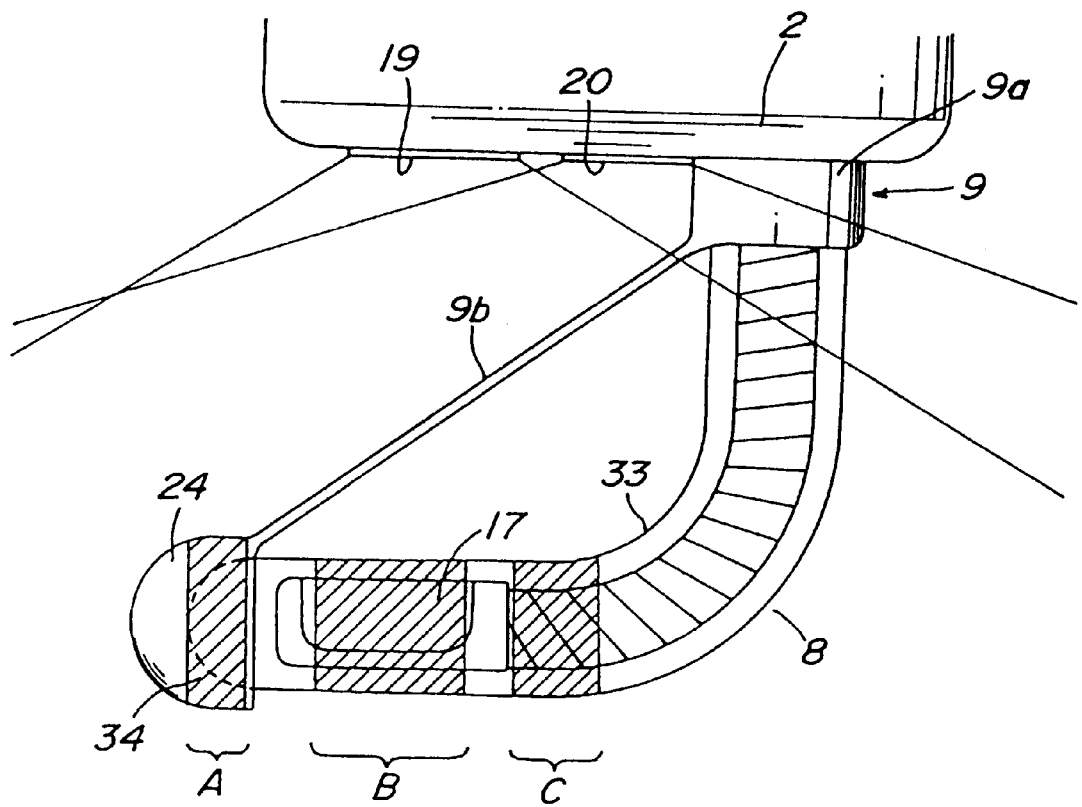
FIG. 12 is an explanatory view showing the utilizing state of eighth embodiment of the bending sheath according to the present invention.

FIG. 12 shows an eighth embodiment of the bending sheath according to the present invention. In this embodiment, at least a part of the cap 24 provided to the tip portion of the outer sheath 9a is provided with a reflecting portion 34 formed by making a surface roughness large. There is an utilization of a worked surface caused by a sand blast working, a working by file and a lathe working as a means of making a surface roughness large. The utilization of worked surface by the lathe working is particularly effective since the variation of reflected light is very large according to the observation angle.

The position of the reflecting portion 34 is not limited to the position of the cap 24 (A position), the position corresponding to the ultrasonic transducer 17 of a sheath 33 (B position), and the position near the ultrasonic transducer 17 of a sheath 33 (C position) may be used. In the case of B position, the bending angle of the place where the ultrasonic transducer 17 transmits and receives the ultrasonic wave can be grasped. While in case of providing the reflecting portion 34 to the sheath 33, if the sheath 33 is formed by resin, the surface lapping is performed due to chemical etching such as tetra-etching treatment or the like for Teflon.

Instead of the reflecting portion 34 grasping a bending ability due to dark and bright of the reflected light, it may utilize a reflecting portion grasping the bending ability by the color change with the use of prism. In this case, the prism changes the color of the reflected light from red to purple by receiving the illuminating light of the endoscope 2, so that the bending ability can be grasped by recognition of the color.

Alternatively, a mirror formed by aluminum deposition is used as the reflecting portion. The other construction is the same as that of first embodiment, so that its detailed explanation is omitted.

The function and effect of this embodiment constructed as described above is described hereinafter. That is, when the bending sheath combined with the ultrasonic probe 8 is inserted in the forceps channel of the endoscope 2 and is projected from the tip portion thereof. The ultrasonic probe 8 is further inserted for the bending sheath 9 and the tip portion thereof is abutted to the cap 24, thereby bending its tip portion.

In this case, the angle of the reflecting portion 34 provided to the cap 24 is changed in accordance with the bending of the ultrasonic probe 8. This reflecting portion 34 receives the illumination of the illumination system 20 of the endoscope 2, so that the operator observes the reflection extent or reflection rate (brightness) of the reflected light by the observation optical system 19. The reflection rate of the reflecting portion 34 is changed by the observation angle because of high surface roughness. For example, this reflection brightness is dark for small bending angle and is bright for large bending angle. Then, the operator grasps the angle of the cap 24, to which the reflecting portion 34 is provided, that is, the bending rate of the ultrasonic probe 8, by the reflection brightness of the reflecting portion 34 obtained by endoscope image.

As described above, in this embodiment as in the same manner as the first embodiment, the tip portion of the probe can be bent only by forcibly inserting the probe such as ultrasonic probe for the bending sheath. The bending angle of the probe tip portion can also be adjusted easily by adjusting the insertion amount of the probe for the bending sheath.

Further, the cap 24 is provided with the reflecting portion 34, so that the bending degree of the tip the ultrasonic probe 8 can be grasped by the reflection rate of the reflecting portion 34. In this point, it is also possible to grasp the bending rate by recognizing the insertion amount of the inserted ultrasonic probe 8 with a scale or the like at the proximal end of the bending sheath 9. However, this scaling method has a defect that it is difficult to coincide the insertion amount at the proximal end with the bending rate because of long ultrasonic probe 8, so that the bending rate can not be grasped properly.

Figure 13:
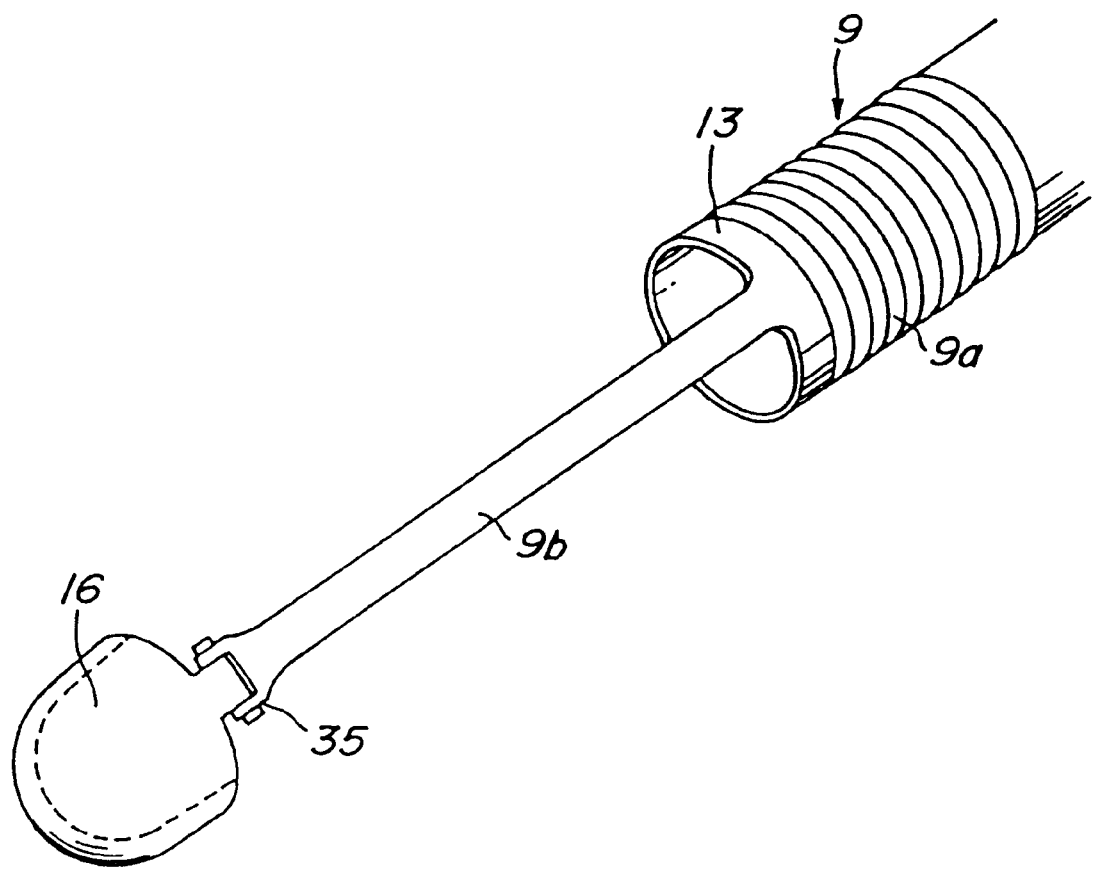
FIG. 13 is a partial perspective view showing ninth embodiment of the bending sheath according to the present invention.
Figure 14:
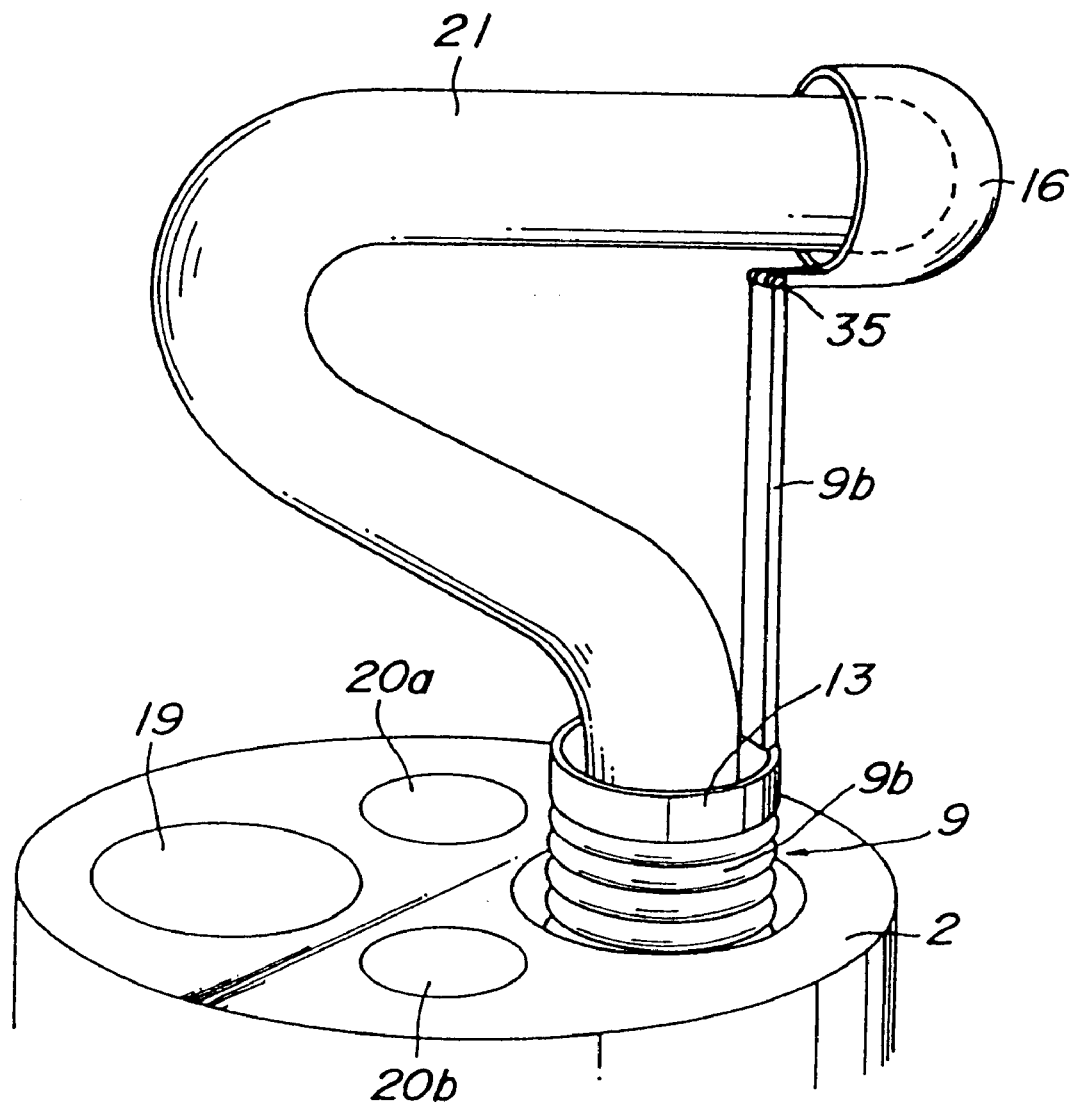
FIG. 14 is a perspective view showing the utilizing state of ninth embodiment of the bending sheath according to the present invention.

FIGS. 13 and 14 show a ninth embodiment of the bending sheath according to the present invention. In this embodiment, a fixing base 13 having a stainless extended portion 9b formed integrally thereto is provided to the tip portion of an outer sheath 9a by soft soldering or hard soldering. The tip of the extended portion 9b is rotatably provided with a cap 16 through a link mechanism 35.

As long as safety and strength are obtained for living body, the extended portion 9b may be formed by titanium, aluminum, copper, iron which are subjected to a surface treatment, in addition to stainless metal. The outer sheath 9a may be formed by a resin tube and a torque tube, in addition to the coil sheath. The link mechanism 35 also can be formed by a hinge capable of being rotated through a fulcrum axis, but may be formed by forming partial recess with the use of resin such as polypropylene, resulting in a bendable construction. The other construction is the same as that of the first embodiment, so that its detailed explanation is omitted.

The function and effect of this embodiment constructed as described above Is described hereinafter. That is, when the probe is inserted for bending sheath, the tip portion of the probe is abutted to the inner wall of the cap portion 16, and when the probe is further inserted forcibly for the bending sheath, it is biased to the cap 16, so that the tip portion of the probe 21 is bent, as shown in FIG. 14.

This is further explained concretely. The cap 16 is rotated by the link mechanism 35 according to the insertion of the probe 21, so that the probe 21 is bent according to this rotation in such a manner that it is pushed out from the bending sheath 9. Therefore, the probe can be observed at the center of the field of the observation optical system 19.

As described above, in this embodiment as in the same manner as the first embodiment, the tip portion of the probe can be bent only by forcibly inserting the probe such as ultrasonic probe for the bending sheath. The bending angle of the probe tip portion can also be adjusted easily by adjusting the insertion amount of the probe for the bending sheath.

Furthermore, the cap 16 can be held on the axis line of the outer sheath 9a through the link mechanism 35, so that when it is used by inserting it in the endoscope, the bending state of the probe 31 can be recognized at the center of the endoscope field.

The extended portion 9b is formed by stainless steel and thus has high stiffness compared with the extended portion consisting of resin, so that the width of the extended portion 9b can be made narrow and the position changing the direction of the cap 16 can be determined by the link mechanism 35.

Figure 15:
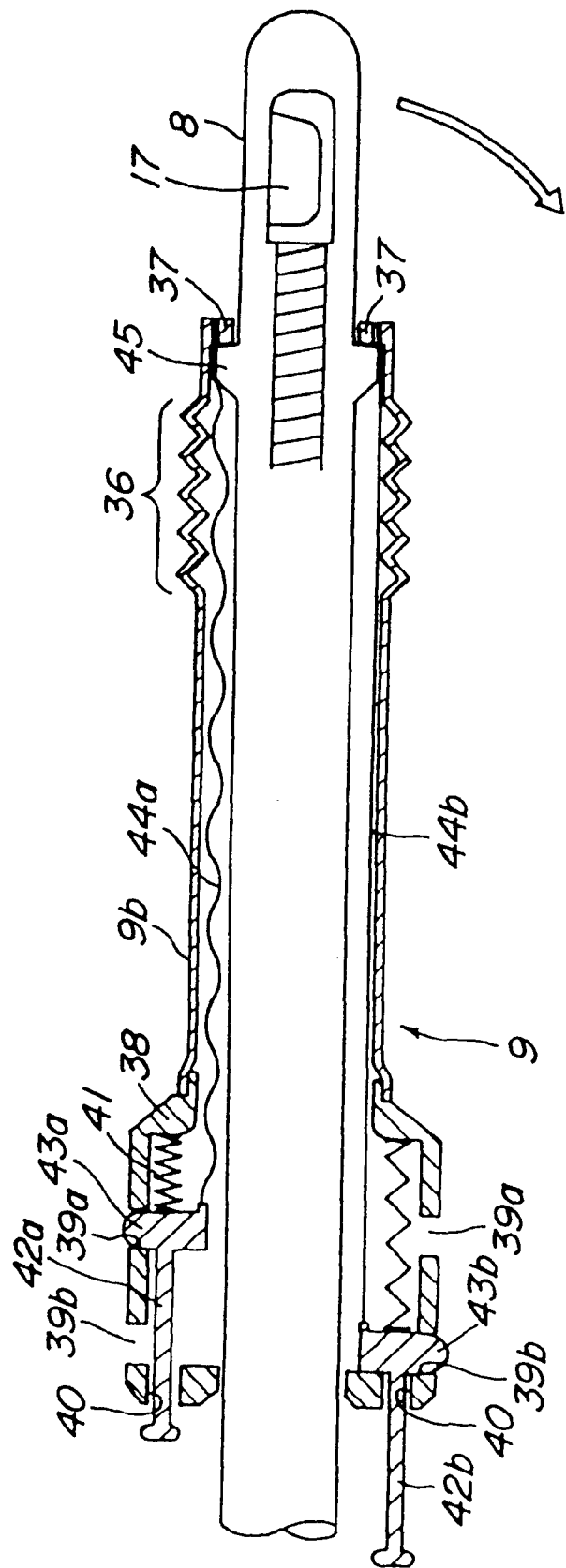
FIG. 15 is a sectional view showing tenth embodiment of the bending sheath according to the present invention.

FIG. 15 shows an tenth embodiment of the bending sheath according to the present invention. In this embodiment, an outer sheath 9a is formed by Teflon and a bellows portion 36 and an iris stop 37 are formed at outside of the tip portion of the outer sheath 9a. The proximal end of the outer sheath 9a is provided with a frame 38, to which first hole 39a, second hole 39b and a guide hole 40 are formed. The frame 38 is provided at its inside with a spring 41 and two manipulatable bars 42a and 42b biased by the spring 41 are also provided in the frame 38. These manipulatable bars 42a and 42b are respectively provided with projections 43a and 43b formed integrally thereto. These projections 43a and 43b can be engaged to and released from the first hole 39a and second hole 39b in accordance with movement of these manipulatable bars 42a and 42b.

These manipulatable bars 42a and 42b are secured to first wire 44a and second wire 44b, respectively, and the other ends thereof are secured to the stop 37. The length of these wires is set in such a manner that the wire is equal to the length under the state in which it is stretched in substantially straight form in the outer sheath 9a, in case of engaging the projections 43a, 43b formed to the manipulatable bars 42a and 42b to the second hole 39b.

In this embodiment, two wires are provided, so that the bending can be obtained in two directions, but the bending may be obtained it three or more directions by decreasing the number of wire. Moreover, when the construction capable of being bent in three or more directions is obtained, the special bending direction can be net by selecting two optional wires simultaneously. Also, in order to select the bending direction, the wire biasing the extension of the bellows 36 may be selected, but to this end, the manipulatable bar corresponding to the wire must be selected. However, the present invention is not limited to the means for selecting the manipulatable bar, the other means for selecting the wire may be utilized.

Moreover, a flange 45 is formed near the tip portion of the ultrasonic probe 8 so as to engage it to the stop 37 of the bending sheath 9. The ultrasonic transducer 17 is positioned prior to the flange 45.

The function and effect of this embodiment constructed as described above is explained hereinafter. The ultrasonic probe 8 is inserted in the bending sheath in such a manner that the flange 45 is abutted to the stop 37. Then, if the direction to be bent by the ultrasonic probe 8 is the arrow direction, the manipulatable bars 42b is projected from the frame 38 and the projection 43b is engaged in the second hole 39b, thereby obtaining the stretched state of the wire 44b. In this case, the other manipulatable bars 42a is forcibly inserted in the frame 38 and the projection 43a is engaged in the first hole 39a, thereby obtaining the slackened state of the wire 44a.

Then, it the ultrasonic probe 8 is further inserted in the bending sheath 9, the bellows 36 is made extended, but is biased by the wire 44b only in one direction so that the tip portion of the ultrasonic probe 8 is bent in the arrow direction.

As described above, in this embodiment as in the same manner as the first embodiment, the tip portion of the probe can be bent only by forcibly inserting the probe such as ultrasonic probe for the bending sheath.

Furthermore, in case of combining the bending sheath of this embodiment to the endoscope, the tip portion of the probe can be bent by selecting the wire to be biased while confirming the bending direction within the field of the endoscope, without utilizing the method of rotating the bending sheath.

When the ultrasonic probe 8 is also used as a probe, the probe is bent at the place of the bellows 36 at the tip of the bending sheath, so that the defect that the extended portion prevents the transmission and reception of the ultrasonic wave, can be avoided and the ultrasonic image can be obtained over 360 degrees.

Figure 16:
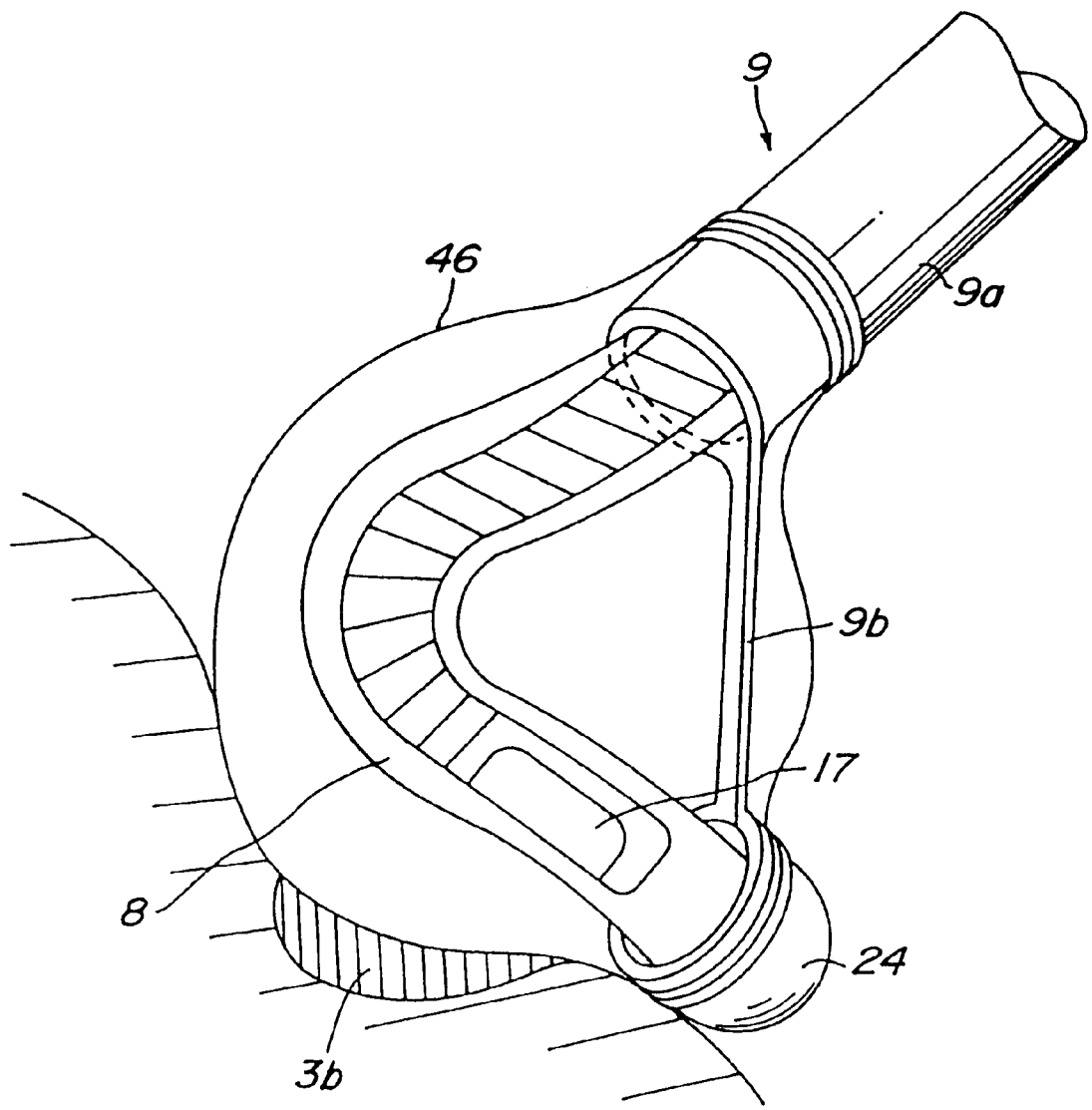
FIG. 16 in a perspective view showing the utilizing state of tenth embodiment of the bending sheath according to the present invention.

FIG. 16 shows an eleventh embodiment of the bending sheath according to the present invention. In this embodiment, an extended portion 9b is provided by notching a part of an outer sheath 9a, and the tip thereof is provided with a cap 24 by thermal forming. Moreover, a balloon 46 is provided so as to cover the outside of the extended portion 9b by using the tip of the outer sheath 9a and the cap 24 as a fixing member. The other construction of the bending sheath is the same as that of the first embodiment, so that its detailed explanation is omitted.

The function and effect of this embodiment constructed as described above is explained hereinafter. The ultrasonic probe 8 is inserted in the bending sheath 9 having the balloon 46 provided thereto until the tip of the ultrasonic probe 8 is abutted to the cap 24. This is inserted in the body cavity through the forceps channel of the endoscope.

Next, deaerated water is injected in the balloon 46 through the outer sheath 9a, thereby inflating the balloon. Under the state that the balloon 46 is inflated in the proper volume, when the ultrasonic probe 8 is further inserted for the bending sheath, the tip portion of the probe 8 is bent in such a manner that the tip portion is pushed out in the transverse direction as shown in FIG. 16, thereby changing the transmission and reception angle of the ultrasonic wave. Under this condition, the endoscope is treated and the ultrasonic probe 8 is closed to the diseased portion 3a of the patient 3 through the balloon 46, and then the ultrasonic wave is transmitted and received.

As described above, in this embodiment as in the same manner as the first embodiment, the tip portion of the probe can be bent only by forcibly inserting the probe such as ultrasonic probe for the bending sheath. The bending angle of the probe tip portion can also be adjusted easily by adjusting the insertion amount of the probe for the bending sheath.

Moreover, the balloon 46 is provided, so that the distance between the bent ultrasonic probe and the wall of the living body can be held constantly, and thus, the ultrasonic probe 8 can hold the distance to the living body constant, thereby obtaining well ultrasonic image. Moreover, by combining the bending sheath and the forward-viewing endoscope, the ultrasonic diagnosis due to a balloon method can be performed under the state that the diseased portion of the patient is front-viewed.

As the probe to be combined to the bending sheath, a thermotherapy probe and a probe in the case of cancer therapy due to laser burn out may be utilized in addition to the ultrasonic probe 8.

What is claimed is:

1. A bending sheath comprising:
    a hollow sheath comprising a sheath tip portion;
    at least one extended portion integrally formed with and extending in a sheath axis direction of the hollow sheath from the sheath tip portion; and
    a tip holding member having a first end which is attached to the at least one extended portion and a second end which is closed to form a shape of a cap; and
    the at least one extended portion comprises a bendable section which bends to cause an end portion of said extended portion to be at an angle relative to the sheath axis direction.

2. A bending sheath as claimed in claim 1, wherein the hollow sheath is a tube comprising by a soft resin.

3. A bending sheath as claimed in claim 2, wherein the soft resin comprises polytetrafluoroethylene.

4. A bending sheath as claimed in claim 2, wherein the soft resin comprises a high-density polyethylene or a low-density polyethylene or a mixed polyethylene thereof.

5. A bending sheath as claimed in claim 2, wherein the soft resin comprises a polyimide resin or a polyolefin resin.

6. A bending sheath as claimed in claim 1, wherein the bendable section is located near the tip holding member and said angle is approximately 90 degrees.

7. A bending sheath as claimed in claim 1, wherein the second end which is closed to form a shape of a cap has a substantially hemispherical shape.

8. A bending sheath as claimed in claim 7, wherein the cap comprises stainless steel.

9. A bending sheath as claimed in claim 1, wherein the hollow sheath comprises by a rotatable coil shaft.

10. A bending sheath as claimed in claim 1, wherein the hollow sheath comprises a rotatable torque transmission tube of resin.

11. A bending sheath comprising:
a hollow sheath comprising a sheath tip portion;
at least one extended portion extending in a sheath axis direction of the hollow sheath from the sheath tip portion; and
a tip holding member having a first end which is attached to the at least one extended portion and a second end which is closed to form a shape of a cap; wherein
the at least one extended portion is formed so as to bend near the tip holding member, and the at least one extended portion comprises:
a wide portion adjacent to the hollow sheath; and
a narrow portion adjacent to the tip holding member.

12. A bending sheath comprising:
a hollow sheath comprising a sheath tip portion;
at least one extended portion extending in a sheath axis direction of the hollow sheath from the sheath tip portion; and
a tip holding member having a first end which is attached to the at least one extended portion and a second end which is closed to form a shape of a cap; wherein
the at least one extended portion is formed so as to bend near the tip holding member; and
the at least one extended portion comprises:
a portion of low flexibility adjacent to the hollow sheath; and
a portion of high flexibility adjacent to the tip holding member.

13. A bending sheath comprising:
a hollow sheath comprising a rotatable coil shaft and sheath tip portion;
at least one extended portion extending in a sheath axis direction of the hollow sheath from the sheath tip portion; and
a tip holding member attached to the at least one extended portion;
wherein the rotatable coil shaft comprises multiple coil shaft layers, each of the multiple coil shaft layers comprising a helical coil comprising multiple wires.

14. A bending sheath as claimed in claim 13, wherein the coil shaft comprises three coil shaft layers, each of the three coil shaft layers comprising a helical coil comprising five wires.

15. A bending sheath comprising:
a hollow sheath comprising a rotatable torque transmission tube and a sheath tip portion;
at least one extended portion extending in a sheath axis direction of the hollow sheath from the sheath tip portion; and
a tip holding member attached to the at least one extended portion;
wherein the rotatable torque transmission tube comprises resin and an embedded metal, silk, and cotton mesh or net member.

16. A bending sheath comprising:
a hollow sheath comprising a sheath tip portion;
at least one extended portion extending in a sheath axis direction of the hollow sheath from the sheath tip portion; and
a tip holding member attached to the at least one extended portion;
wherein the tip holding member comprises a reflecting portion.

17. A bending sheath as claimed in claim 16, wherein the reflecting portion is formed by making a surface roughness large.

18. A bending sheath as claimed in claim 16, wherein the reflecting portion is a prism.

19. A bending sheath as claimed in claim 16, wherein the reflecting portion is a mirror.

20. A bending sheath comprising:
a hollow sheath comprising a sheath tip portion;
at least one extended portion extending in a sheath axis direction of the hollow sheath from the sheath tip portion;
a tip holding member; and
a link mechanism for rotatably connecting the tip holding member to the at least one extended portion.

21. A probe assembly comprising:
a probe comprising a tip portion and an apparatus for irradiating energy having directivity; and
a bending sheath into which the probe is inserted, the bending sheath comprising:
a hollow sheath comprising a sheath tip portion;
at least one extended portion extending in a sheath axis direction of the hollow sheath from the sheath tip portion; and
a tip holding member for detachably holding the tip portion, the tip holding member having a first end which is attached to the at least one extended portion and a second end which is closed to form a shape of a cap.

22. A bending sheath as claimed in claim 21, wherein the apparatus for irradiating energy inserted in the bending sheath is a ultrasonic probe or a laser probe.

23. A probe assembly comprising:
a probe comprising a tip portion and a treating unit of a punch biopsy; and
a bending sheath into which the probe is inserted, the bending sheath comprising:
a hollow sheath comprising a sheath tip portion;
at least one extended portion extending in a sheath axis direction of the hollow sheath from the sheath tip portion; and
a tip holding member for detachably holding the tip portion, the tip holding member having a first end which is attached to the at least one extended portion and a second end which is closed to form a shape of a cap.

24. A bending sheath comprising:
a hollow sheath comprising a sheath tip portion;
at least one extended portion integrally formed with and extending in a sheath axis direction of the hollow sheath from the sheath tip portion;

a tip holding member attached to the at least one extended portion;

a balloon provided between the hollow sheath and the tip holding member; and the at least one extended portion comprises a bendable section which bends to cause an end portion of said extended portion to be at an angle relative to the sheath axis direction.

25. A bending sheath as claimed in claim 24, wherein the balloon encloses the at least one extended portion.

* * * * *